(12) United States Patent
Mougin et al.

(10) Patent No.: US 7,343,270 B2
(45) Date of Patent: Mar. 11, 2008

(54) METHOD FOR MODELING ASPHALTENES FLOCCULATION CONDITIONS IN HYDROCARBON-CONTAINING FLUIDS RELATED TO A REFERENCE FLUID

(75) Inventors: Pascal Mougin, Rueil Malmaison (FR); Annabelle Pina, Poissy (FR); Sophie Jullian, Rueil Malmaison (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 634 days.

(21) Appl. No.: 10/376,303

(22) Filed: Mar. 3, 2003

(65) Prior Publication Data

US 2003/0167157 A1 Sep. 4, 2003

(30) Foreign Application Priority Data

Mar. 1, 2002 (FR) .................................. 02 02667

(51) Int. Cl.
*G06F 17/10* (2006.01)
(52) U.S. Cl. ............................................ 703/2; 703/10
(58) Field of Classification Search ................ 703/2, 703/10
See application file for complete search history.

(56) References Cited

OTHER PUBLICATIONS

E. Behar et al.; "Integration of Asphaltenes Flocculation Modeling into Athos Resevoir Simulator", 2003, Oil & Gas Science and Technology, vol. 58, No. 6.*

Xiangjun Qin et al., "Modeling Asphaltene Precipitation in Resevoir Simulation", 2000, Ind. Eng. Chem. Res., vol. 39, No. 8, pp. 2644-2654.*

Y.-F. Hu et al., "A study on the application of scaling equation for asphaltene precipitation", Fluid Phase Equilibria, vol. 171, pp. 181-195.*

Compositional Model For Predicting Asphaltenes Flocculation-Fluid Phase Equilibria, V. Szewcyk et al, vol. 158-160, 1999, pp. 451-469.

Edmonds et al "A Unified Framework For Calculating Solid Deposition From Petroleum Fluids Including Waxes, Asphaltenes, Hydrates and Scales" Fluid Phase Equilibria, vol. 158-160, 1999, pp. 481-489.

Hirschberg et al "Influence of Temperature and Pressure On Asphaltene Flocculation" Society of Petroleum Engineers Journal, Dallas, Texas US, vol. 24, No. 3, Jun. 1984 pp. 283-293.

(Continued)

*Primary Examiner*—Paul Rodriguez
*Assistant Examiner*—Russ Guill
(74) *Attorney, Agent, or Firm*—Antonelli, Terry, Stout & Kraus, LLP (57) ABSTRACT

Method for modeling the flocculation conditions of hydrocarbon-containing fluids under pressure, related to a reference fluid. The asphaltenic properties are modeled from the results of an experimental study of a single asphaltenic reference fluid and by means of homothetic transformation laws. These reduced data allow to deal with asphaltenes flocculation in an industrial simulator working according to a simplified model. It is then possible to predict the amounts of asphaltenes that will flocculate in a reservoir or in a reactor during development, considering the variable pressure and composition conditions. Application: optimization of the development conditions of reservoirs or of an industrial reactor in which asphaltenic fluids undergo expansions.

16 Claims, 4 Drawing Sheets

OTHER PUBLICATIONS

Abdoul et al "Group-Contribution Equation Of State For Correlating And Predicting Thermodynamic Properties Of Weakly Polar and Non-Associating Mixtures. Binary and Multicomponent Systems" Fluid Phase Equilibria, Elsevier Scientific Publishing Company, Amsterdam, NL vol. 68 1991 pp. 47-102.

Cimino et al "Thermodynamic Modelling For Prediction Of Asphaltene Deposition In Live Oils" No. 18993 Feb 14, 1995, pp. 499-512.

Hotier et al "Action of Various Diluents On Heavy Petroleum Products: Measurement, Interpretation, and Prediction of Asphaltene Flocculation" Revue de l'Institut Francais du Petrole, Editions Technip, Paris, France, vol. 38 No. 18, 1983 pp. 101-120.

* cited by examiner

METHOD FOR MODELING ASPHALTENES FLOCCULATION CONDITIONS IN HYDROCARBON-CONTAINING FLUIDS RELATED TO A REFERENCE FLUID

FIELD OF THE INVENTION

The present invention relates to a method for modelling the flocculation of asphaltenes in hydrocarbon-containing fluids during a depletion phase.

The method according to the invention allows to produce a computer tool for predicting asphaltenes flocculation risks that can be readily integrated in an industrial simulator. It can be, for example, a reservoir simulator, which is one of the major pieces used by operators to evaluate the production of oil or gas fields, their life and their production mode (primary, secondary or tertiary). It can also be a basin simulator. These simulators are designed to predict the behaviour of a field or of a petroliferous region over a long period. The quality of the simulators depends on their capacity to best reproduce the various physical phenomena that occur during the production of hydrocarbons, such as for example the nature and the composition of the various phases involved, the flow of the material flux and the interactions of the fluids with the porous medium forming the reservoir. The simulators available on the market are equipped to predict the evolution of many possible phenomena. However, one of them is currently difficult to take into account: asphaltenes flocculation.

BACKGROUND OF THE INVENTION

Figure 1:
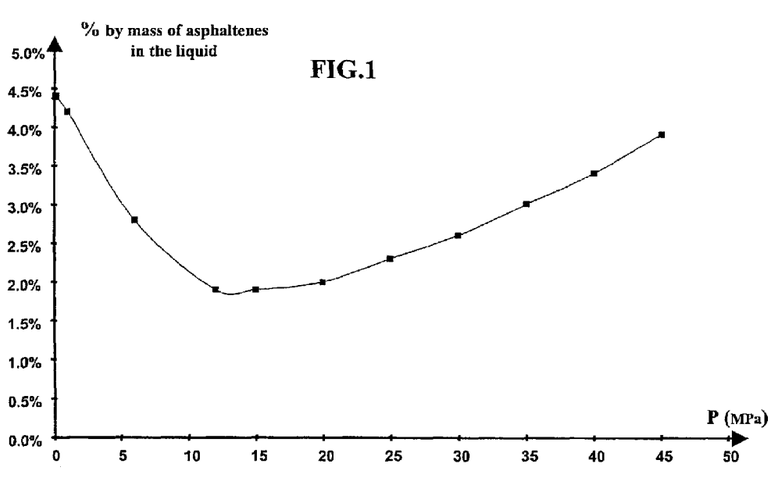
FIG. 1 shows the course of a pressure flocculation curve.

Asphaltenes are the heaviest and the most polar components of a petroleum cut. A petroleum fluid is in fact a continuous series of hydrocarbons (alkanes, naphthenes, aromatics). Asphaltenes are defined, according to the French AFNOR T 60-115 standard, as the fraction of a petroleum fluid that flocculates (precipitates) in n-heptane and is soluble in benzene. It is therefore a solubility class. These asphaltenes flocculate under the effect of three factors: temperature, pressure or chemical composition variation. FIG. 1 shows the behaviour of an asphaltenic crude under pressure.

This curve shows the amount of asphaltenes in the liquid fluid after a possible flocculation. When the pressure decreases, the amount of asphaltenes falls, which proves that part of the asphaltenes has flocculated. Flocculation is maximum (and the amount of asphaltenes in the liquid minimum) when the bubble-point pressure (appearance of the first vapour bubble) is reached. Below this pressure, the appearance of a vapour phase rich in alkanes and therefore in flocculating products allows the liquid to become asphaltenes-friendly again.

A change in the composition of the fluid can also induce the flocculation phenomenon. Addition of light alkanes produces flocculation of the asphaltenes, whereas addition of aromatics allows to stabilize them in the crude.

During production of a well, the hydrocarbon-containing fluid undergoes pressure, temperature and composition variations. It is therefore likely to flocculate. This flocculation is translated into the deposition of asphaltenes in the pores of the reservoir, which consequently leads to a change in the porosity of the medium, in its permeability and eventually in the hydrocarbons production. In extreme cases, this flocculation can cause clogging of the pores and lead to close the well. It is therefore important to be able to predict this phenomenon.

The following publications are representative of the state of the art:

Hirschberg L., De Jong B., Schipper J., Meijer J., Soc. Pet. Eng. J., June, 283 Paper No.11202, 1984, Mansoori G., Jiang T., $3^{rd}$ European Conference on Enhanced Oil Recovery, Rome, April 1985, or Szewczyk V., Béhar E., Compositional model for predicting asphaltenes flocculation, Fluid Phase Equilibria, 156-160, pp. 459-469, 1999.

None of the many flocculation models described in the open literature has a predictive character. Basically, all these representations consider a conventional model for representing the liquid-vapour behaviour of the hydrocarbon-containing fluid. Flocculation is described, but there are no means of predicting the flocculation phenomenon. Certain models consider asphaltenes as solid particles suspended in the crude and flocculation is represented by a colloidal model. In another thermodynamic approach, asphaltenes are considered to be a new liquid phase. The appearance of a liquid or solid phase, according to the aforementioned authors, therefore has to be controlled. All these models require experimental data such as those of FIG. 1 for example in order to be used.

In order to account for the pressure and composition variation, two approaches can be considered. The first one consists in having a rather detailed compositional model of the fluid and a flocculation curve. It is then possible to extrapolate the model in the domain close to the calibration domain of the model. The second method consists in determining flocculation curves as a function of the pressure for different fluid compositions so as to be able to generate a family of flocculation curves in the domain of interest. These two approaches appear to be unusable in practice within the context of industrial simulation softwares. The first approach is difficult to implement because a detailed compositional model of the fluid has to be included in these simulators, which is very costly in computing time. The second approach is also too costly, but in experimentation time: acquisition of data relative to flocculation under pressure is long and delicate, and it is not possible to accumulate curves for a large number of fluid compositions.

SUMMARY OF THE INVENTION

We provide here an alternative method which allows, from the results of an experimental study of the flocculation under pressure of a single reference fluid and from homothetic transformation laws, to deduce very simply the curves relative to the flocculation under pressure of related fluids, obtained from the reference fluid. These related fluids result from the depletion of the reference fluid. The method according to the invention allows integration of a flocculation model in an industrial simulator according to a simplified model. These homothetic transformation laws can be obtained by using a detailed compositional model or by means of more general laws according to the accepted uncertainty degree.

The method according to the invention thus consists in experimentally studying an asphaltenic fluid under pressure in order to deduce its precise behaviour. It is then possible to model this fluid, then to study this model so as to define the homothetic parameters required for prediction of the flocculation curves of related fluids. This simple homothetic model and the experimental curve of the reference fluid are then integrated in an industrial simulator. It is then possible to predict the amounts of flocculated asphaltenes for variable pressure and composition conditions. For example, in a reservoir simulator, these asphaltenic deposits will lead to a change in the reservoir permeability and to a production change. Taking account of the asphaltenes flocculation will thus allow to better simulate the life of the hydrocarbons reservoir and the productivity of the wells for example.

The method according to the invention can be readily translated in form of a processing module (preprocessor) suited to generate a library of depletion flocculation curves from an experimental curve. In a reservoir simulator, this preprocessor can be specific to each field studied, all the more so since the flocculation curve of the reference fluid can be extrapolated under conditions close to calibration, or more generic from the analysis of a larger number of oil fields. In fact, the family of curves can be, for example, normalized by the bubble-point pressure and the asphaltenes amounts. The homothetic transformation formulas obtained can then be generalized and extrapolated from one petroleum fluid to another.

In other words, the method according to the invention allows to model the conditions of flocculation under pressure of related hydrocarbon-containing fluids from a reference fluid. It essentially comprises the following stages:

measuring experimentally the pressure flocculation curve of the reference fluid, determining homothetic transformation laws allowing to obtain the corresponding flocculation curves of the related fluids, and determining the flocculation risks of asphaltenes in the reference fluid during treatments requiring pressure changes, by using the flocculation curves obtained by applying these homothetic transformation laws.

According to a first embodiment, homothetic transformation laws are determined by means of the following stages:

applying to the reference fluid a detailed compositional model to determine its asphaltenic behaviour, simulating compositions of related fluids from the reference fluid, determining a series or library of flocculation curves of the related fluids by using the model, defining homothetic transformation parameters necessary for prediction from the library of flocculation curves of the related fluids.

According to another embodiment, homothetic transformation laws are determined by using a general model of homothetic transformation laws using norms such as the bubble-point pressure and the maximum amounts of flocculated asphaltenes or any other macroscopic quantity readily accessible by the experimenter.

The method comprises for example applying flocculation data to an industrial simulator to determine flocculation appearance conditions.

The method also allows to determine the impact of flocculation on the physico-chemical properties of the medium surrounding the fluid.

The flocculation risks of the related fluids can be determined for example by applying flocculation data to an industrial simulator applying a simplified compositional model.

The method also allows to determine the permeability variation of the reservoir.

Application of the method, using the homothetic properties of the flocculation curves, allows to spare long and tedious studies of the related fluids resulting from expansions or depletions applied to fluids under pressure likely to flocculate.

BRIEF DESCRIPTION OF THE DRAWINGS

Other features and advantages of the method and of the device according to the invention will be clear from reading the description hereafter of an embodiment given by way of non limitative example, with reference to the accompanying drawings wherein.

DETAILED DESCRIPTION

Figure 2:
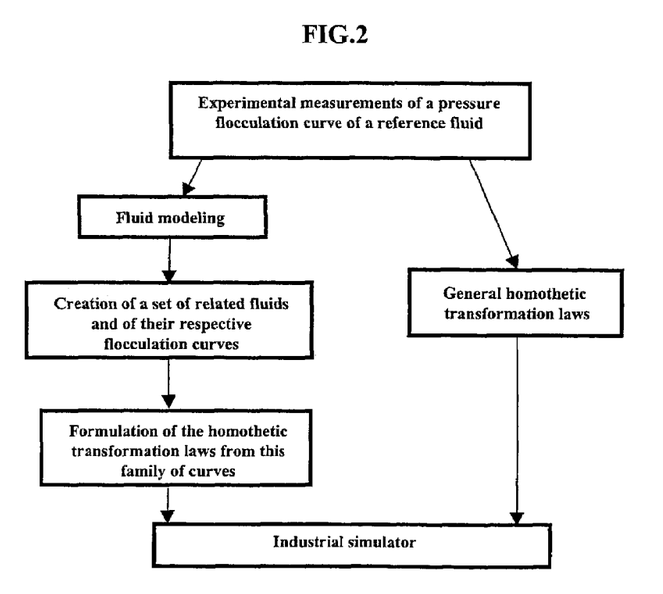
FIG. 2 diagrammatically shows the method according to the invention.

A flowchart of the method according to the invention is shown in FIG. 2. An experimental study of the reference fluid is carried out first. This fluid can be a reservoir fluid, a heavy residue or any other hydrocarbons mixture likely to induce flocculation of the asphaltenes under pressure. In addition to the conventional PVT study, it is necessary to obtain pressure flocculation data, i.e. to measure the amount of asphaltenes deposits according to the pressure. This study can for example be carried out by pressure filtration of the reservoir fluid. Homothetic transformation laws are then applied to model the asphaltenic behaviour of related fluids (also called son fluid in the description) resulting from expansion of the reference fluid (or parent fluid). These laws can be obtained in two different ways as described hereafter.

1) Homothetic Transformation Laws Using a Compositional Model

From experimental data obtained on this reference fluid, it is possible to model it from an asphaltenic point of view by using a detailed compositional model.

Figure 3:
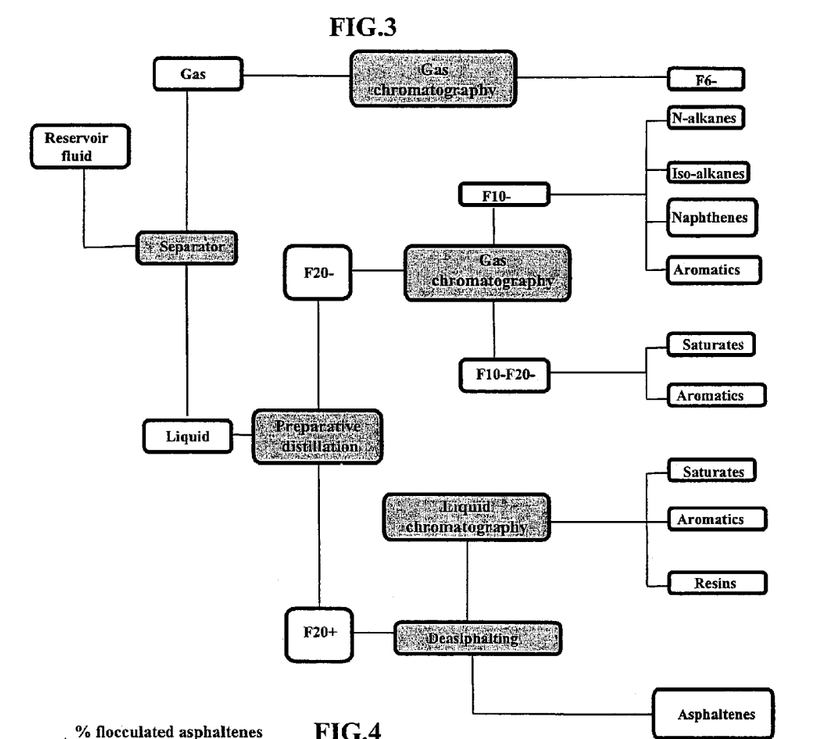
FIG. 3 shows the fractionation of a petroleum fluid according to the analysis protocol described by Szewczyk and Béhar.

The model provided by Szewczyk and Béhar (1999) in the aforementioned publication can for example be used. This model is based on a detailed description of the fluid as shown in FIG. 3. For the hydrocarbons of the F6 fraction, each molecule is perfectly identified. For the hydrocarbon fraction between F6 and F10, each family of isomers is represented by a type molecule. For the F11-F20 fraction, a pseudo-constituent is characterized from analytical data and group contribution methods. Finally, the four F20+ fractions: saturates, aromatics, resins and asphaltenes are each represented by a pseudo-compound whose properties are provided by group contribution methods. This compositional model is then coupled to liquid-liquid-vapour phase equilibrium calculations. The appearance of a second liquid phase represents the asphaltenes phase. To calculate these equilibria, the authors use Peng and Robinson's equation coupled to Abdoul and Péneloux's mixture laws, well-known to the man skilled in the art, i.e.:

$$P = \frac{RT}{v-b} - \frac{a(T)}{v(v+\gamma b)}$$

with: v: the uncorrected molar volume
b: the covolume
a(T): the interaction parameter.

In a standard way, P is the pressure of the system, T its temperature, R is the perfect gas constant and γ is a constant whose value is 4.82843 for Peng and Robinson's equation. The expression of a(T) is written in the following form:

$$A(T) = a(T_c)\alpha(T_R, \omega)$$

with:

$$a(T_C) = 0.45724 \frac{R^2 T_C^2}{P_C} \qquad \alpha(T_R, \omega) = (1 + m(1 - T_R^{0.445}))^2$$

$$m = \frac{\sqrt{1.12754 + 0.51725\omega - 0373\omega^2} - 1}{1 - 0.7^{0.445}} \qquad T_R = \frac{T}{T_C}$$

The covolume is defined as:

$$b = 0.04557 \frac{RT_C}{P_C}$$

The « true » molar volume, V, is obtained by a translation of volume c:

$$V = v - c$$

where:

$$c = (0.08315 - 0.4406 Z_{RA}) \frac{RT_C}{P_C}$$

$Z_{RA}$ is Rackett's compressibility factor.

All these definitions are valid for pure bodies. For a mixture, each body i has its own critical properties $a_i$, $b_i$, $c_i$, defined as above. To consider the whole of the mixture as a single constituent following the same formalism, mixture rules are applied to the critical properties of the pure bodies to acquire the global parameters of the system a, b, c. Abdoul and Péneloux's laws are used in this model. The following references provide the details of this model:

Abdoul, W., 1987, Une méthode de contribution de groupes applicable à la corrélation et la prédiction des propriétés thermodynamiques des fluides pétroleirs, Thése de l'université d'Aix-Marseille III, France; and Péneloux, A., Abdoul, W. and Rauzy, E., Excess functions and equation of state, Fluid Phase Equilibria, 47, 115.

Knowing the thermodynamic modelling of the reference fluid, it is then possible to generate the detailed compositions of related fluids resulting from expansion. These related fluids can thereafter be studied as regards the flocculation of asphaltenes with the thermodynamic model. A pressure flocculation curve library is thus generated for the reference fluid and the related fluids. The next stage consists in determining quite general variation laws for the whole of the library. For example, these laws can be polynomial functions of the bubble-point pressure, of the gas-oil ratio or of any other operating quantity readily accessible by the experimenter.

Figure 4:
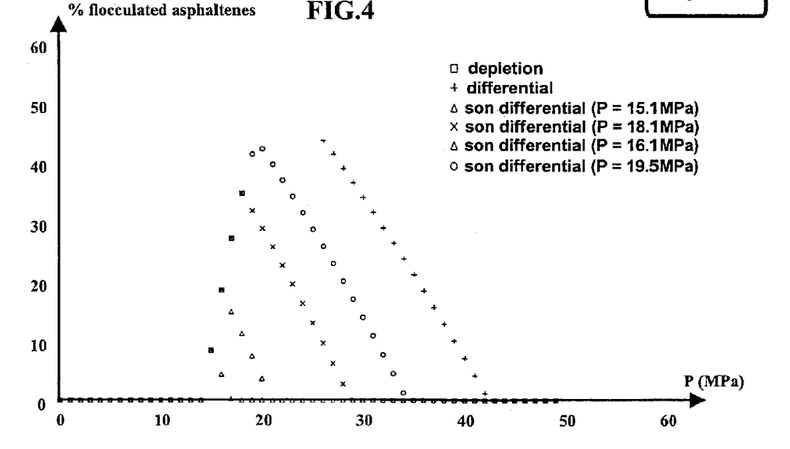
FIG. 4 shows the course of the family of flocculation curves of a first crude.
Figure 5:
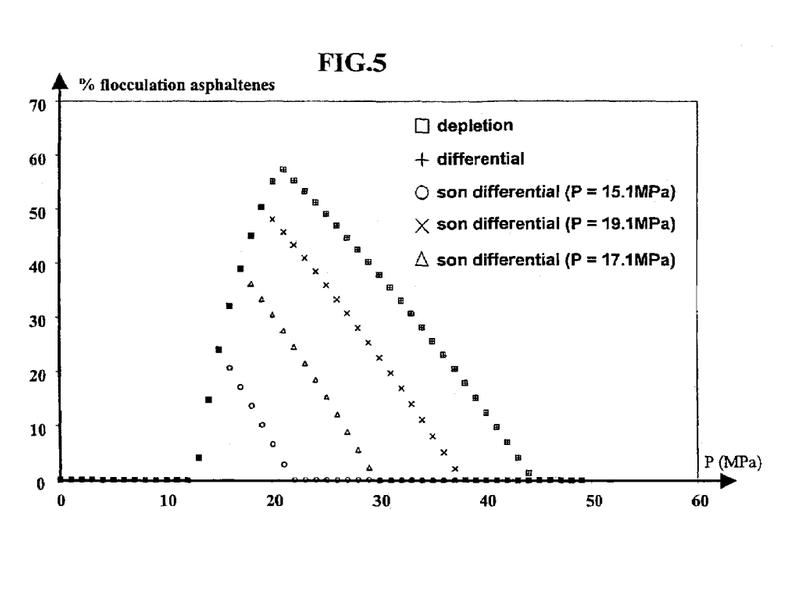
FIG. 5 shows the course of the family of flocculation curves of a second crude.

It has been observed on various fluids that the whole of the flocculation curves forms a family of homothetic curves; FIGS. 4 and 5, which show the evolution of the proportion of asphaltenes flocculated with the pressure in the case of two fluids undergoing differential experiments (release of an associated gas during an expansion), illustrate these results.

2) General Homothetic Transformation Laws

Figure 6:
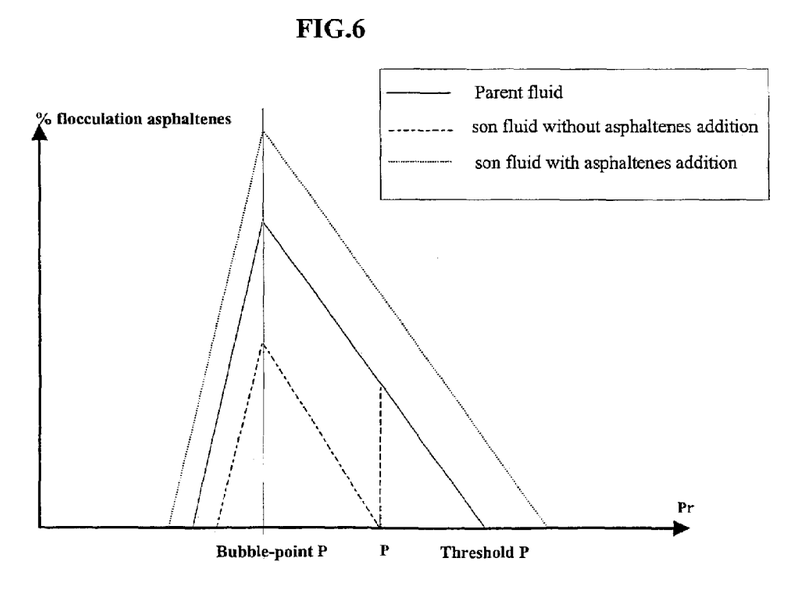
FIG. 6 shows examples of flocculation curves for a reference fluid and two associated related fluids when they are produced at a pressure above the bubble-point pressure.

Application of the method described in the previous paragraph has shown that the curve families can be normalized by the amount of asphaltenes present and by the bubble-point pressure. This leads us to propose more general homothetic transformation laws that can represent the pressure flocculation curves of related fluids. For example, we consider a curve giving the asphaltenes flocculated as a function of the pressure (curve of the reference fluid in FIG. 6). For a pressure P ranging between the flocculation threshold pressure (threshold P) and the bubble-point pressure, the reference fluid leads to the creation of an asphaltenes deposit and of a related fluid. If no asphaltenes are added to this related fluid, it will have pressure P as the flocculation threshold pressure. If we assume that the amount of asphaltenes does not influence the bubble-point pressure, the related fluid thus has the same bubble-point pressure as the reference fluid. At this stage, there are two ways of calculating the maximum of the flocculation curve of the related fluid. The first one consists in writing that:

$$\max = \frac{\text{parent max flocculated amount} - \text{flocculated amount}}{\text{total partent asph. amount} - \text{flocculated amount}}$$

The second way considers that the slope of the flocculated asphaltenes curve as a function of the pressure is kept, whence:

max=parent max flocculated amount—flocculated amount

If the related fluid comes into contact with new asphaltenes (asph.sup pl.), the maximum amount of flocculated asphaltenes can then be calculated as follows:

$$\max = \frac{\text{parent max flocculated amount} - \text{flocculated amount} + \text{asph. sup pl}}{\text{total parent asph amount} - \text{flocculated amount} + \text{asph. sup pl.}}$$

Under such conditions, the slope of the flocculation curve of the reference fluid is kept to estimate the flocculation threshold pressure. For pressures below the bubble-point pressure, a homothetic transformation is carried out from this bubble-point pressure and from the maximum amount of asphaltenes. FIG. 6 summarizes this modelling possibility.

Figure 7:
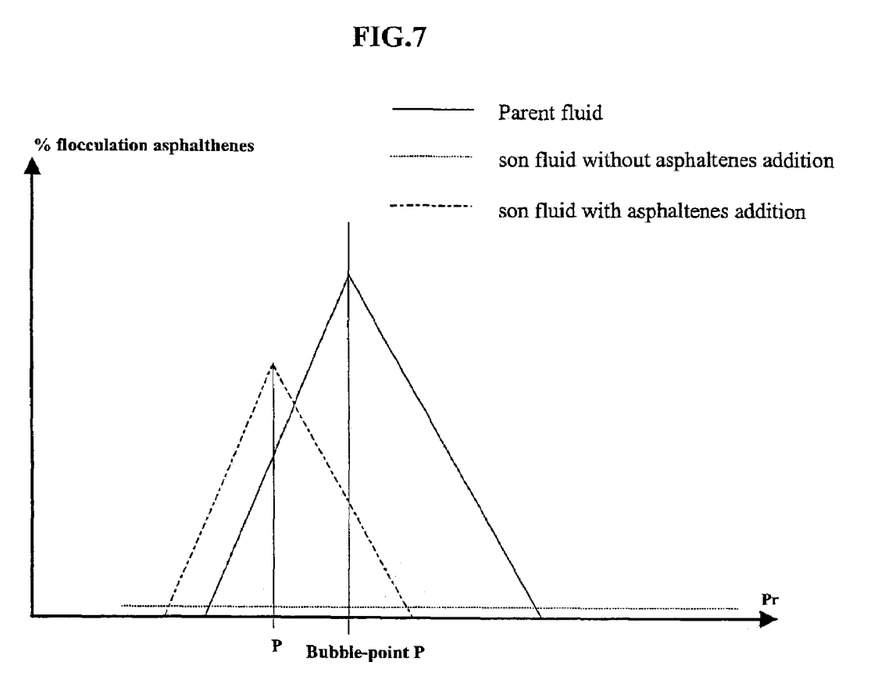
FIG. 7 shows examples of flocculation curves for a reference fluid and two associated related fluids when they are produced at a pressure below the bubble-point pressure.

Let us now assume that expansion of the initial fluid occurs at a pressure below the bubble-point pressure. The related fluid produced thus has a bubble-point pressure equal to the expansion pressure. If no asphaltenes are added to this fluid, it is stable for pressures above its bubble-point pressure. Below its bubble-point pressure, the fluid is also stable towards asphaltenes: if its pressure is decreased, flocculants continue to be released and the fluid is thus made more and more solvent towards asphaltenes. On the other hand, if asphaltenes are added, the new maximum of the flocculation curve is calculated as follows (where soluble asph.: soluble asphaltenes):

$$\max = \frac{\text{asph. sup pl.}}{\text{soluble asph.+asph. sup pl.}}$$

The same slopes as those of the reference fluid are kept to obtain the flocculation thresholds. FIG. 7 shows these two cases.

The homothetic transformation laws defined above thus allow to represent a series of flocculation curves for related fluids from the experimental curve of the reference fluid. This approach can be integrated in an industrial simulator where the information required for a detailed representation is not available: the fluids are often described, in a simplified way, as comprising only some constituents: water, a heavy hydrocarbon constituent and a light hydrocarbon constituent for example (black-oil model). On the other hand, these approaches include the material balance and bubble-point pressure information, and the method according to the invention can be perfectly integrated in this procedure. The aforementioned computing time problems for complex compositional models are not present. The only obligatory experimental datum of this model is the pressure flocculation curve of the reference fluid. It is thus possible to estimate the pressure flocculation curves of the related fluids resulting from depletion.

The method allows to determine the amounts of asphaltenes that flocculate at the various stages of the development of a field or of a reservoir for example.

This information can then be directly used for example for modelling the porosity change of the reservoir. By using conventional Karman-Kozemy type equations, well-known to specialists, the permeability variation of the medium can be predicted. This has a direct impact on the production of the field.

The method can be applied to optimization of the development conditions of reservoirs or of an industrial reactor in which asphaltenic fluids undergo expansions.

The invention claimed is:

1. A method for determining flocculation risks of asphaltenes in a reference fluid by modelling conditions of flocculation of hydrocarbon-containing fluids under pressure for related fluids resulting from pressure reduction or depletion of the reference fluid, comprising the following stages:
   measuring experimentally a pressure flocculation curve of the reference fluid;
   defining homothetic transformation laws allowing to obtain corresponding flocculation curves of the related fluids;
   integrating the homothetic transformation laws and the pressure flocculation curve of the reference fluid in an industrial simulator applying a simplified compositional model; and
   determining flocculation risks of asphaltenes in the reference fluid during treatments requiring pressure changes, by using the industrial simulator.

2. A method as claimed in claim 1, characterized in that the homothetic transformation laws are determined using the following stages:
   applying to the reference fluid a detailed compositional model to determine its asphaltenic behaviour;
   simulating compositions of related fluids from the reference fluid;
   determining a series or library of flocculation curves of the related fluids by using the detailed compositional mode;
   defining homothetic transformation parameters necessary for prediction from the library of flocculation curves of the related fluids.

3. A method as claimed in claim 1, characterized in that homothetic transformation laws are determined by using a general model of homothetic transformation laws using bubble-point pressure or maximum amounts of flocculated asphaltenes.

4. A method as claimed in claim 1, further comprising applying flocculation data to the industrial simulator in order to determine flocculation appearance conditions.

5. A method as claimed in claim 4, characterized in that an impact of flocculation on the physico-chemical properties of a medium surrounding the reference fluid is determined.

6. A method as claimed in claim 1, further comprising optimizing development conditions of a reservoir based on the flocculation risks determined.

7. A method as claimed in claim 1, further comprising optimizing development conditions of an industrial reactor based on the flocculation risks determined.

8. A method as claimed in claim 1, further comprising optimizing development conditions of a reservoir or an industrial reactor based on the flocculation risk determined.

9. A method for modeling the amounts of asphaltenes that flocculate in a reference fluid at the various stages of the development of a field during treatments requiring pressure changes, comprising the following stages:
   measuring experimentally a pressure flocculation curve of the reference fluid;
   defining homothetic transformation laws allowing to obtain corresponding flocculation curves of related fluids resulting from pressure reduction or depletion of the reference fluid;
   integrating the homothetic transformation laws and the pressure flocculation curve in an industrial simulator applying a simplified compositional model; and
   determining the amounts of asphaltenes that flocculate in the reference fluid, by using the industrial simulator.

10. A method as claimed in claim 9, characterized in that the homothetic transformation laws are determined using the following stages:
    applying to the reference fluid a detailed compositional model to determine its asphaltenic behaviour;
    simulating compositions of related fluids from the reference fluid;
    determining a series or library of flocculation curves of the related fluids by using the detailed compositional mode; and
    defining homothetic transformation parameters necessary for prediction from the library of flocculation curves of the related fluids.

11. A method as claimed in claim 9, characterized in that homothetic transformation laws are determined by using a general model of homothetic transformation laws using bubble-point pressure or maximum amounts of flocculated asphaltenes.

12. A method as claimed in claim 9, characterized in that an impact of flocculation on the physico-chemical properties of a medium surrounding the reference fluid is determined.

13. A method as claimed in claim 9, further comprising predicting asphaltene deposits by means of a reservoir simulator.

14. A method as claimed in claim 9, further comprising determining conditions of flocculation of hydrocarbon-containing fluids under pressure for the related fluids, and optimizing development conditions of a reservoir based on the said conditions of flocculation.

15. A method as claimed in claim 9, further comprising determining conditions of flocculation of hydrocarbon-containing fluids under pressure for the related fluids, and optimizing development conditions of an industrial reactor based on the said conditions of flocculation.

16. A method as claimed in claim 9, further comprising optimizing development conditions of a field by predicting asphaltene deposits, by means of a reservoir simulator, at various stages of development of the field during treatments requiring pressure changes.

* * * * *